United States Patent [19]

Cotton

[11] 4,082,611

[45] Apr. 4, 1978

[54] CONTINUOUS FERMENTATION PROCESS

[75] Inventor: Neil Trevor Cotton, St. Agnes near Truro, England

[73] Assignee: Imperial Chemical Industries Limited, London, England

[21] Appl. No.: 746,015

[22] Filed: Nov. 30, 1976

[51] Int. Cl.² .............................................. C12B 1/00
[52] U.S. Cl. ................................... 195/28 R; 195/49; 195/115
[58] Field of Search ................ 195/115, 49, 28 R, 123

[56] References Cited

U.S. PATENT DOCUMENTS 3,834,989   9/1974   Harrison .............................. 195/28 R Primary Examiner—Lionel M. Shapiro
Attorney, Agent, or Firm—Cushman, Darby & Cushman

[57] ABSTRACT

A process for the continuous production of single cell protein in which liquid handling costs are reduced by treating the culture in order to kill a proportion of the microorganisms present. Various treatments may be used to kill the microorganisms but treatment with formaldehyde is preferred.

9 Claims, 1 Drawing Figure

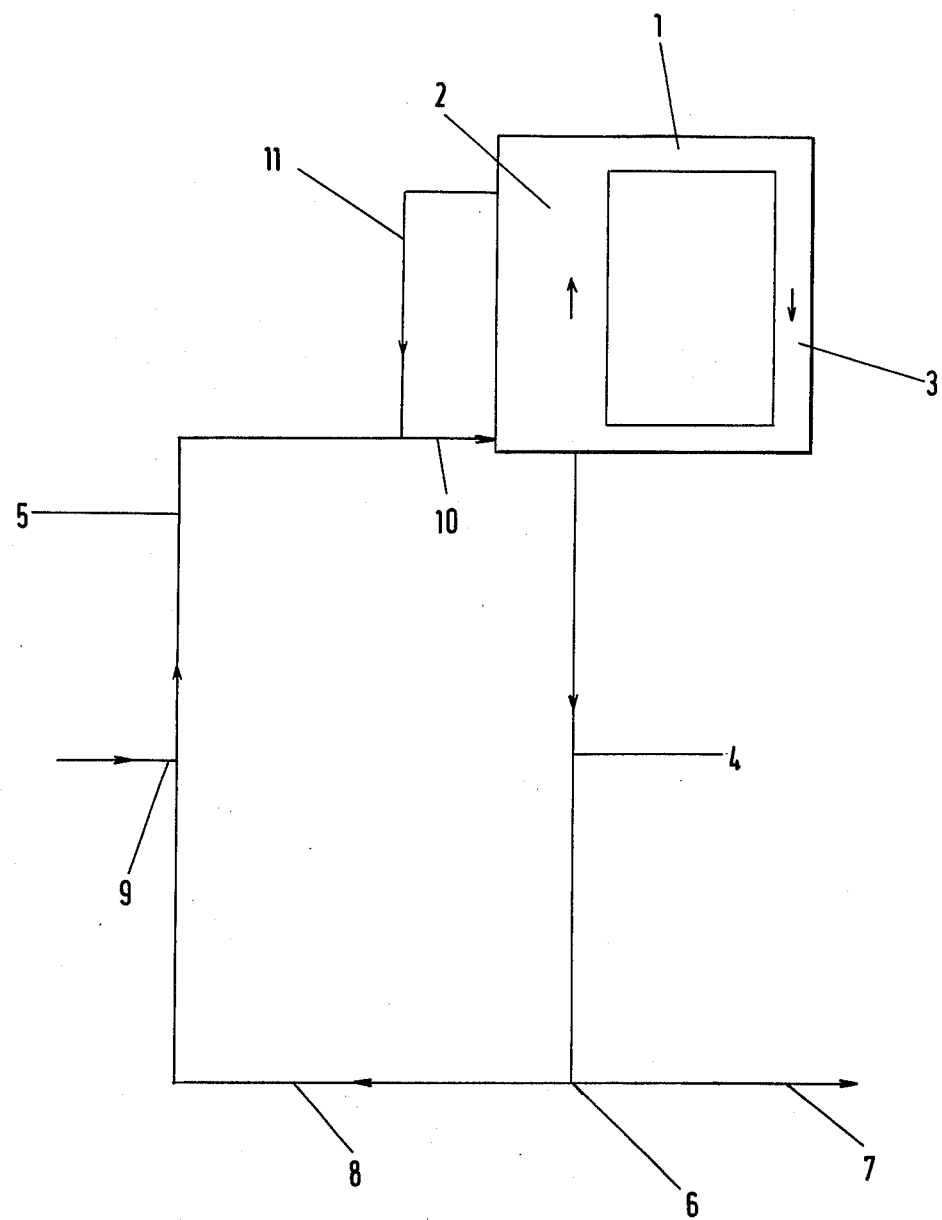

CONTINUOUS FERMENTATION PROCESS

This invention relates to a fermentation process and in particular to a process for the production of single cell protein by continuous fermentation.

In a continuous fermentation process for the production of single cell protein it is important that the rate of production of dried cells after harvesting and drying should be maintained at a high level in order to avoid excessive liquid handling and recycling costs. However the total productivity of a process for producing single cell protein is limited by the oxygen transfer capacity of the system in which the process is operated. Thus in operating such a process upon a commercial scale the system must have an oxygen transfer capacity sufficiently great to avoid excessive liquid handling and recycling costs.

According to the present invention we provide a fermentation process for continuously culturing microorganisms upon a medium comprising a source of assimilable carbon and inorganic nutrients wherein the culture is continuously treated in order to kill a proportion of the microorganisms present during culturing.

Preferably the fermentation process is a process for the production of single cell protein, particularly by culturing yeasts or bacteria upon media containing hydrocarbons or alcohols such as methanol as sources of assimilable carbon. The present invention is particularly suitable for carrying out the process of our UK Specification No. 1 370 892 in which bacteria belonging to the species *Pseudomonas methylotropha, Hyphomicrobium variabile, Microcyclus polymorphum* or *Pseudomonas rosea* are cultured. The characteristics of these species are described in our UK Specification No. 1 370 892. Preferred microorganisms for use in the process of this specification are *Pseudomonas methylotropha* strains, particularly those strains deposited at the following culture collections:

a. National Collection of Industrial Bacteria, Torry Research Station, Aberdeen, Scotland, UK (NCIB)
b. U.S. Department of Agriculture, Peoria, Ill., USA (NRRL)
c. Fermentation Research Institute, Japan (FERM)

and given the following culture collection numbers:
a. NCIB 10508-15 and 10592-6
b. NRRL B 5353-64
FERM 1215-27.

Suitably the proportion of microorganisms killed is such that, when the fermentation is proceeding in its steady state, 20 to 70%, particularly about 50%, of the microorganisms present in the culture are dead.

Any known means may be used for killing the microorganisms. Suitable means include a high temperature shock at for example 50°–65° C, subjection to $\gamma$ - radiation, a pH shock at for example pH<4.5 or > 8.0 or treatment with formaldehyde. Treatment with formaldehyde is preferred since this reagent is an efficient sterilant at low temperatures of both vegetative cells and spores and can be metabolised by many microorganisms and can thus be kept at a limiting concentration, e.g 1 to 2 ppm, in a carbon-limited system. For example formaldehyde can be co-metabolised, ie it can be metabolised in the presence of another carbon source, by strains of *Pseudomonas methylotropha* which convert methanol via formaldehyde to formic acid and then to carbon dioxide. Preferably cells which are treated are killed absolutely and 'maimed' cells are either not produced or are produced in minimal proportions. When formaldehyde is used it is preferably added to the medium entering the fermentation process in proportions between 0.1 and 5.0% (levels of 0.5 to 1.0% will usually be sufficient to kill a satisfactory proportion of the microorganisms).

The invention is illustrated by the Example which is described with the aid of the accompanying drawing.

EXAMPLE

The drawing shows in diagramatic form a process operated in accordance with the present invention. The fermentation is performed in a fermenter 1 of our UK Specification Nos. 1 353 008; 1 417 486 or 1 417 487 and has a riser 2 and downcomer 3. In the fermenter which has a volume of 1000 liters the circulation rate of the culture is about 30 $M^3$/hr, the dilution rate D is 0.1 $hrs^{-1}$ and the culture contains 30 gms/l of live cells plus 30 gms/l of dead cells. The microorganisms belong to a strain of *Pseudomonas methylotropha* and the carbon source is methanol.

From the fermenter culture containing 6% solids is removed along line 4 to be harvested at 6. Harvesting may be performed by the method of our UK Specification No. 1 381 306. From harvesting stage 6 30 liters/hr of liquid containing 200 g/liter of cells passes along line 7 to a drier (not shown in the drawing) whilst 70 liters/hr of recycle medium containing no cells passes along line 8. At point 9 on line 8 there is added to the recycle medium fresh medium containing methanol and inorganic nutrients together with formaldehyde. The fresh medium is added in proportions such that the flow of recycle and fresh medium along line 5 is at the rate of 100 liters/hr and the combined media contain 1% formaldehyde and 11% methanol.

From the fermenter there is a culture recycle along line 11 whereby culture at the rate of 100 liters/hr is fed into recycle line 5. Thus the concentration of formaldehyde in part 10 of the recycle line is half its concentration in line 5, namely 0.5%.

In this system equal volumes of medium and fermenter culture are mixed at a point where the medium is already sterile. During passage along line 10 the formaldehyde kills the microorganisms. When the fermenter is being operated at a steady state this leads to 50% of the microorganisms present in the culture in the fermenter being dead. So long as the formaldehyde is fully metabolised by the microorganisms none will remain in the culture medium and the product will be the same as that produced in in the absence of the formaldehyde.

A 60 gms/l feed of cells into line 4 gives a maximum recycle of 70% (cf 85% on a 30 gm/l feed). This is half the recycle achieved in a conventional system and leads to a much reduced chance of a build up of inorganic nutrients in the culture medium.

We believe that such a system will produce the following advantages:

1. No necessity for heat sterilization once culturing is continuous.
2. Reduced heat exchanger fouling problems.
3. Liquid volume flows halved.
4. Reduced % recycle.
5. The same dissolved oxygen tansion (DOT) profile as in a conventional system.
6. Marginally reduced ash content of final product.

I claim:

1. A fermentation process for continuously culturing microorganisms in a culture medium containing a source of assimilable carbon and inorganic nutrients which comprises the steps of continuously withdrawing a proportion of the culture from the main body thereof, treating the withdrawn culture to kill microorganisms present therein and returning the treated culture to the main body of the culture, the proportion of the microorganisms killed being such that, when the fermentation is proceeding in its steady state, 20 to 70% of the microorganisms present in the main body of the culture are dead.

2. A process according to claim 1 wherein the proportion of microorganisms killed is such that about 50% of the microorganisms in the culture are dead.

3. A fermentation process for continuously culturing microorganisms in a culture medium containing a hydrocarbon or an alcohol as a source of assimilable carbon and inorganic nutrients, said process including the steps of:

treating the withdrawn culture with formaldehyde to kill microorganisms present therein, and returning the treated culture to the main body of the culture by adding formaldehyde to the medium as it enters the fermentation process in an amount between 0.1 and 5.0%, the proportion of the microorganisms killed being such that, when the fermentation is proceeding in its steady state, 20 to 70% of the microorganisms present in the main body of the culture are dead.

4. A process according to claim 1 wherein the carbon source is a hydrocarbon or an alcohol.

5. A process according to claim 4 wherein the carbon source is methanol.

6. A process according to claim 5 wherein the microorganisms are bacteria belonging to the species *Pseudomonas methylotropha*.

7. A process according to claim 6 wherein the bacteria belong to a strain selected from the group consisting of NRRL Nos. B 5352 to B 5364.

8. A process according to claim 1 wherein the microorganisms which are killed are killed by treatment with formaldehyde.

9. A process according to claim 8 wherein formaldehyde is added to the medium entering the fermentation process in proportions between 0.1% and 5.0%.

* * * * *